US011679134B2

(12) United States Patent
Kim et al.

(10) Patent No.: US 11,679,134 B2
(45) Date of Patent: Jun. 20, 2023

(54) **PHARMACEUTICAL COMPOSITION, FOOD COMPOSITION AND FOOD ADDITIVE FOR PREVENTING, ALLEVIATING OR TREATING MUSCLE LOSS, WEAKNESS AND ATROPHY, CONTAINING, AS ACTIVE INGREDIENT, *ENTEROCOCCUS FAECALIS*, CULTURE LIQUID THEREOF OR DEAD CELLS THEREOF**

(71) Applicants: KOREA BERM CO., LTD., Seoul (KR); UNIVERSITY INDUSTRY FOUNDATION, YONSEI UNIVERSITY WONJU CAMPUS, Wonju-si (KR); NIHON BERUMU CO., LTD., Tokyo (JP)

(72) Inventors: Tack Joong Kim, Wonju-si (KR); Myung Hun Lee, Siheung-si (KR); Masahiro Iwasa, Tokyo (JP); Kwon il Han, Seoul (KR); Wan Jae Kim, Seoul (KR)

(73) Assignees: KOREA BERM CO., LTD., Seoul (KR); UNIVERSITY INDUSTRY FOUNDATION, YONSEI UNIVERSITY WONJU CAMPUS, Wonju-si (KR); NIHON BERUMU CO., LTD., Tokyo (JP)

( * ) Notice: Subject to any disclaimer, the term of this patent is extended or adjusted under 35 U.S.C. 154(b) by 146 days.

(21) Appl. No.: 16/757,279

(22) PCT Filed: Oct. 18, 2017

(86) PCT No.: PCT/KR2017/011557
§ 371 (c)(1),
(2) Date: Apr. 17, 2020

(87) PCT Pub. No.: WO2019/078381
PCT Pub. Date: Apr. 25, 2019

(65) Prior Publication Data
US 2021/0046127 A1   Feb. 18, 2021

(51) Int. Cl.
*A61K 35/744* (2015.01)
*A23L 29/00* (2016.01)
*A23L 33/135* (2016.01)
*A61K 9/00* (2006.01)
*A61K 9/14* (2006.01)
*A61K 9/20* (2006.01)
*A61K 9/48* (2006.01)
*A23L 33/16* (2016.01)
*A23L 33/155* (2016.01)

(52) U.S. Cl.
CPC .......... *A61K 35/744* (2013.01); *A23L 29/015* (2016.08); *A23L 29/035* (2016.08); *A23L 29/045* (2016.08); *A23L 33/135* (2016.08); *A23L 33/155* (2016.08); *A23L 33/16* (2016.08); *A61K 9/0019* (2013.01); *A61K 9/14* (2013.01); *A61K 9/2059* (2013.01); *A61K 9/4866* (2013.01)

(58) Field of Classification Search
CPC ...... A61K 35/744; A61K 9/0019; A61K 9/14; A61K 9/2059; A61K 9/4866; A23L 29/015; A23L 29/035; A23L 29/045; A23L 33/135; A23L 33/155; A23L 33/16
See application file for complete search history.

(56) References Cited

FOREIGN PATENT DOCUMENTS

| JP | 2003261453 | 9/2003 |
| KR | 1020060108964 | 10/2006 |
| KR | 1020140070794 | 6/2014 |
| KR | 1020140082964 | 7/2014 |
| KR | 1020170123122 | 11/2017 |

OTHER PUBLICATIONS

Gu et al., Medicine and Biology, 2007, vol. 15, No. 9, p. 289-294.*
Lieffers et al., British Journal of Cancer, 2012, vol. 107, p. 931-936.*

* cited by examiner

*Primary Examiner* — Kade Ariani
(74) *Attorney, Agent, or Firm* — MH2 Technology Law Group, LLP (57) ABSTRACT

The present invention relates to a pharmaceutical composition, a food composition, and a food additive for the prevention and treatment or improvement of muscle loss, muscle weakness, and muscle atrophy, which contain *Enterococcus faecalis*, particularly *Enterococcus faecalis* EF-2001 among others, a culture solution thereof, or a killed body thereof as an active ingredient. Killed *Enterococcus faecalis* EF-2001 of the present invention exhibits a remarkable treatment effect for muscle loss, muscle weakness, and muscle atrophy by inhibiting the damage to muscle cells induced by oxidative stress, and thus killed lactic acid bacterium *Enterococcus faecalis* EF-2001 of the present invention or a culture solution thereof can be usefully used as an active ingredient in a pharmaceutical composition, a food composition, and a food additive for prevention of muscle atrophy and sarcopenia.

7 Claims, 5 Drawing Sheets

PHARMACEUTICAL COMPOSITION, FOOD COMPOSITION AND FOOD ADDITIVE FOR PREVENTING, ALLEVIATING OR TREATING MUSCLE LOSS, WEAKNESS AND ATROPHY, CONTAINING, AS ACTIVE INGREDIENT, *ENTEROCOCCUS FAECALIS*, CULTURE LIQUID THEREOF OR DEAD CELLS THEREOF

This application is a National Phase of International Application No. PCT/KR2017/011557 filed on 18 Oct. 2017, which is hereby incorporated herein by reference in its entirety for all purposes.

TECHNICAL FIELD

The present invention relates to novel use of *Enterococcus faecalis*, a culture solution thereof, or a killed body thereof. More specifically, the present invention relates to a pharmaceutical composition, a food composition, and a food additive for the prevention and treatment or improvement of muscle loss, muscle weakness, and muscle atrophy, which contain *Enterococcus faecalis* EF-2001 (deposited under the Budapest Treaty on May 31, 2002, at National Institute of Technology and Evaluation, Shiba, Japan with accession no. NITE EUP-16804), a culture solution thereof, or a killed body thereof as an active ingredient.

BACKGROUND ART

Diseases that cause muscle weakness include sarcopenia which progresses with aging, muscle atrophy which is caused by imbalance in protein metabolism or decreased muscle use, and acardiotrophia which progresses with starvation, wasting diseases (cancer and the like), aging.

Sarcopenia refers to a decrease in muscle strength due to a decrease in skeletal muscle mass during aging. Not only the decrease in skeletal muscle mass, which is the most important feature of sarcopenia, but also changes in the type of muscle fibers is observed. Type 1 and Type 2 decrease with aging at similar rates, whereas Type 2 muscle fiber thickness does not change much but Type 1 muscle fiber thickness decreases significantly when sarcopenia occurs. It has been reported that such sarcopenia causes aging and functional impairment among elderly people (Roubenoff R., Can. J. Appl. Physiol. 26, 78-89, 2001).

Although sarcopenia is caused by various factors, the studies on each factor is still insufficient. Sarcopenia is caused by a reduction in growth hormone or a neurological change, a change in physical activity, a change in metabolism, an increase in a sex hormone level, fat or catabolic cytokines, and a change in the balance of protein synthesis and differentiation (Roubenoff R. and Hughes V A, J. Gerontol. A. Biol. Sci. Med. Sci. 55, M716-M724, 2000). A decrease in satellite cell activation is considered to be an important factor which causes a decrease in skeletal muscle mass which is the most important feature of sarcopenia. Satellite cells are small mononuclear cells located between the basement membrane and the sarcolemma of a muscle fiber. They are activated by stimulation such as injury or exercise to proliferate into myoblasts, and they fuse with other cells to form polynuclear muscle fibers as differentiation progresses. Hence, as the activity of satellite cells decreases, the capability of regenerating damaged muscle or the response to differentiation signals is reduced, resulting in decreased muscle formation.

Meanwhile, muscle atrophy is caused by factors such as damage to muscle tissue due to absence of mechanical stimulation such as decreased muscle use, destruction of muscles due to direct injury or physical factors, impaired resilience of muscle cells due to aging, and impairment of muscle use due to damage to nerves that regulate muscle action (Booth F W., J Appl Physiol Respir Environ Exerc Physiol., 1982). In general, disuse atrophy, which gradually progresses to muscle atrophy, occurs due to loss of muscle strength since muscles in the affected area and surrounding areas are not used for a long time due to a disorder or accident. Muscle atrophy also occurs in the form of myasthenia gravis, dystrophy due to diseases of the muscle itself: progressive muscular dystrophy, myotonic muscular dystrophy, Dusen's type, Becker's type, zone type, facial scapula upper arm type, inflammation of the muscle itself, and spinal muscular amyotrophy, which is an atrophy caused by damage to the nerves that dominate the muscle: Veradnich-Hoffman type, Kugelberg, Belander's disease, amyotrophic lateral sclerosis (ALS): Lou Gehrig's disease, spinobulbar muscular atrophy: Kennedy's disease: and the like.

The interests of people were focused on food, clothing, and shelter in the past, but the interests of people are nowadays more focused on welfare and leisure based on the improved quality of life and enriched living. People are trying to lead a healthy life through exercise. In order to lead such life, free control and use of veterinary muscles are required to be prerequisite, but situations in which veterinary muscles cannot be used due to muscle dysfunction may result in limitation of person's range of activity and deterioration in the quality of life.

There are three main treatment methods for sarcopenia. The first is exercise. Exercise has been reported to increase the protein synthesis ability of skeletal muscle in short term and to increase muscle strength and motility of the elderly. However, it is unsuitable for a long-term treatment (Timothy J. Doherty, J. Appl. Physiol. 95, 1717-1727, 2003). The second is medication, and testosterone or anabolic steroid may be used, but it shows side effects such as inducing virilism in women and prostate symptoms in men, and the like. Other approved therapeutic methods include DHEA (dehydroepiandrosterone) and growth hormone, which have been reported to be useful therapeutic methods at the sites that include SARMs (Selective Androgen Receptor Modulators) (D. D. Thompson, J. Musculoskelet Neuronal Interact 7, 344-345, 2007). Recently, a stem cell therapy in which satellite cells are introduced into the body after the cells are isolated and differentiated in vitro, and a method for maintaining or strengthening muscles by directly activating satellite cells in the body to promote myogenesis have come to the fore as the treatment methods for muscle weakness such as sarcopenia (Shihuan Kuang and Michael A. Rudnicki, Trends in Molecular Medicine 14, 82-91, 2008).

In general, the best thing people can do to prevent the development of muscle atrophy in daily life is to prevent muscle loss through continued use of muscles. However, muscle atrophy due to muscle degeneration may occur even when muscle use is impossible regardless of the person's will, such as an injury or disorder. Even in this case, countermeasures that can prevent muscle atrophy by stimulating muscles or preventing muscle degeneration and the studies thereon are required.

Reactive oxygen species are a group of chemically reactive molecules and substances exhibiting high reactivity due to strong properties for the redox reaction to exchange electrons with surrounding substances. Due to the reactivity of such reactive oxygen species, surrounding substances such as protein molecules and DNA in the cell lose electrons to be oxidized and mutated and are unable to perform the correct function, and cells that are unable to perform the correct function cannot survive, leading to apoptosis. Among the various factors of such stress, oxidative stress caused by reactive oxygen species also appears in muscle cells, and loss of muscle cells and muscle atrophy may be induced by such oxidative stress. Various stress factors have been regarded to affect various tissues in vivo as well as damage to muscle tissue and thus have attracted attention as factors of various diseases (MCKinnell I W., And Rudnicki M A., Cell, 2004).

*Enterococcus faecalis* EF-2001 has been identified by screening intestinal microflora of a 2 years old girl. The *Enterococcus faecalis* EF-2001 is killed by heat treatment and the cell components are recovered to obtain killed *Enterococcus faecalis* EF-2001.

According to studies reporting the physiological activity of *Enterococcus faecalis* EF-2001, in the case of mice suffering from colitis caused by Dextran sulfate sodium (DSS), it has been reported that a DSS relieving effect is exerted in mice who have ingested *Enterococcus faecalis* EF-2001 and proliferation of transplanted sarcoma cancer cells (Sarcoma-180) is reduced and NK cells are activated (Tadano et al., J. Japan Mibyou System association, 2011). In addition, biochemically, in the case of mice who have ingested *Enterococcus faecalis* EF-2001, it has been reported that the ratio of total cholesterol and triglyceride decreases even after the mice have eaten a high fat diet (Ku et al., Medicine and biology, 2007). In addition, with regard to the inhibition of harmful bacteria and intestinal regulation, *Enterococcus faecalis* EF-2001 inhibits the activity of *Candida albicans*, the cause of white coating on tongue, and thus improves and prevents the symptoms (Ishijima et al., Med. Mycol. J, 2014). In mice treated with antibiotics, efficacy of rapidly proliferating beneficial bacteria and inhibiting harmful bacteria as compared to the intestinal control group is disclosed (Simohashi et al., Medicine and biology, 2002). The various physiological activities of *Enterococcus faecalis* EF-2001 have the advantage of being able to be processed into various forms of preparations since they are not affected by heat and pH due to the nature of killed bacteria (Kan, Food industry, 2001). In addition, it is possible to ingest a large amount of lactic acid bacteria even when a small amount of *Enterococcus faecalis* EF-2001-containing material is eaten since the content of *Enterococcus faecalis* EF-2001 is 7.5 trillion bacteria per gram.

Meanwhile, as prior literatures on the treatment for muscle atrophy, Korean Granted Patent No. 1,560,799 discloses a composition for treatment of spinal muscular amyotrophy, which contains hnRNP M (heterogeneous nuclear ribonucleoprotein M) or a polynucleotide encoding the same as an active ingredient, Korean Granted Patent No. 1,468,123 discloses a composition for improvement or treatment of muscle atrophy disease, which contains stem cells derived from mammalian umbilical cord as an active ingredient, Korean Granted Patent No. 1,385,191 discloses a pharmaceutical composition for prevention and treatment of muscle atrophy, which contains extract of *Cichorium intybus* as an active ingredient, and Korean Granted Patent No. 1,349,361 discloses a pharmaceutical composition for prevention and treatment of muscle atrophy, which contains extract of *Eupatorium chinensis* var. simplicifolium as an active ingredient, but the effect of *Enterococcus faecalis*, a culture solution thereof, or a killed body thereof on muscle atrophy has not been known at all.

Accordingly, as a result of efforts to develop a novel medicine for muscle loss, muscle weakness, and muscle atrophy, which does not exhibit cytotoxicity and exhibits reliable safety to the human body, the present inventors have found out that killed *Enterococcus faecalis* EF-2001 does not exhibit cytotoxicity, secures stability in the human body, and exhibits a remarkable muscle loss, muscle weakness, and muscle atrophy treatment effect by inhibiting the damage to muscle cells and apoptosis induced by oxidative stress, and thus completed the present invention.

CITATION LIST

Patent Literature

Korean Granted Patent No. 1560799 (Registration Date 2015 Oct. 8)
Korean Granted Patent No. 1349361 (Registration Date 2014 Jan. 2)

Non Patent Literature

Roubenoff R., Can. J. Appl. Physiol. 26, 78-89, 2001
Roubenoff R. and Hughes V. A., J. Gerontol. A. Biol. Sci. Med. Sci. 55, M716-M724, 2000
D. D. Thompson, J. Musculoskelet Neuronal Interact 7, 344-345, 2007
Shihuan Kuang, and Michael A. Rudnicki, Trends in Molecular Medicine 14, 82-31, 2008
Timothy J. Doherty, J. Appl. Physiol. 95, 1717-1727, 2003
Tadano et al., J. Japan Mibyou System association, 2011
Ku et al., Medicine and biology, 2007
Ishijima et al., Med. Mycol. J, 2014
Simohashi et al., Medicine and biology, 2002
Kan, Food industry, 2001

SUMMARY OF INVENTION

Technical Problem

Hitherto, the use of *Enterococcus faecalis* for the treatment of muscle weakness-related diseases has not been known. Hence, the present invention demonstrates the stability of *Enterococcus faecalis* EF-2001 to the human body and confirms that *Enterococcus faecalis* EF-2001 exhibits a remarkable treatment effect for muscle loss, muscle weakness, and muscle atrophy by inhibiting the damage to muscle cells induced by oxidative stress. Accordingly, an object of the present invention is to demonstrate the treatment efficacy of killed *Enterococcus faecalis* EF-2001 and a culture solution thereof for muscle loss, muscle weakness, and muscle atrophy and to provide a novel pharmaceutical composition, a novel food composition, and a novel food additive for the prevention and treatment of muscle loss, muscle weakness, and muscle atrophy.

Solution to Problem

In order to achieve the above object, the present invention provides a pharmaceutical composition for prevention and treatment of muscle weakness-related diseases containing *Enterococcus faecalis*, a culture solution thereof, or a killed body thereof as an active ingredient.

The present invention also provides a food composition for prevention and improvement of muscle weakness-related diseases containing *Enterococcus faecalis*, a culture solution thereof, or a killed body thereof as an active ingredient.

The present invention also provides a food additive for prevention and improvement of muscle weakness-related diseases containing *Enterococcus faecalis*, a culture solution thereof, or a killed body thereof as an active ingredient.

In addition, the present invention provides a method for treating or preventing muscle weakness-related diseases including administering a pharmaceutically effective amount of *Enterococcus faecalis*, a culture solution, or a killed body thereof to an individual suffering from a muscle weakness-related disease or an individual.

Advantageous Effects of Invention

Killed *Enterococcus faecalis* EF-2001 of the present invention does not exhibit cytotoxicity and exhibits a remarkable treatment effect for muscle loss, muscle weakness, and muscle atrophy by inhibiting the damage to muscle cells induced by oxidative stress, and thus *Enterococcus faecalis* of the present invention, a culture solution thereof, or a killed body thereof can be usefully used as an active ingredient in a composition for prevention or treatment of muscle loss, muscle weakness, and muscle atrophy, a food composition, and a food additive.

DESCRIPTION OF EMBODIMENTS

Hereinafter, the present invention will be described in more detail.

The present invention provides a pharmaceutical composition for prevention and treatment of muscle weakness-related diseases containing *Enterococcus faecalis*, a culture solution thereof, or a killed body thereof as an active ingredient.

The microorganisms of the genus *Enterococcus* are widely present in nature and utilize carbohydrates aerobically. In general, it is known that bacteria, such as microorganisms of the genus *Enterococcus*, prevent damage caused by pathogenic microorganisms by antagonism or secreted antibacterial substances in vivo.

As the *Enterococcus faecalis*, a culture solution thereof, or a killed body thereof, both commercially available products and those prepared by known methods for preparing killed bacteria may be used, and these do not exhibit toxicity and are harmless to the human body.

The culture solution refers to a culture solution in which *Enterococcus faecalis* have been cultured in a culture medium, a concentrated culture solution, a dried product of a culture solution, a culture filtrate, a concentrated culture filtrate, or a dried product of a culture filtrate and may be a culture solution containing the cell strain or a culture filtrate obtained by removing the cell strain after culture.

The killed bacteria can be prepared by subjecting the corresponding live bacteria to a heat treatment or treating the corresponding live bacteria with formalin or other fungicides. The killed bacteria can be used even when they are substantially killed. In addition, the killed bacteria used in the present invention may be prepared by the following method, but the method is not limited to this.

1) A step of subjecting *Enterococcus faecalis* to starter culture and then subjecting the *Enterococcus faecalis* to main culture in a neutral or weakly acidic medium in a temperature range of 20° C. to 40° C.

2) A step of subjecting the culture solution to a heat treatment after the main culture of 1) and then drying the culture solution.

The "muscle weakness" means a state in which the strength of one or more muscles have decreased. The muscle weakness may be limited to any one muscle, one side of the body, the upper limbs or the lower extremities or may occur throughout the body. In addition, subjective muscle weakness symptoms including muscle fatigue or muscle pain can be quantified by an objective method through physical examination.

The muscle weakness-related diseases mean all diseases which can be developed due to muscle weakness, and examples thereof include, but are not limited to, sarcopenia or muscle atrophy.

The sarcopenia refers to a gradual decrease in skeletal muscle mass with aging and means a state in which a decrease in muscle strength is directly caused and, as a result, various physical functions may be diminished and disorders may occur.

The muscle atrophy is preferably muscle atrophy due to the loss of muscle tissue caused as muscles are not used, muscle atrophy due to the disease of muscle itself, or muscle atrophy due to the damage to nerves which dominate muscles. The muscle atrophy due to the loss of muscle tissue caused as muscles are not used is more preferably disuse atrophy, the muscle atrophy due to the disease of muscle itself is more preferably myasthenia gravis or dystrophy, and the muscle atrophy due to the damage to nerves which dominate muscles is more preferably spinal muscular amyotrophy, amyotrophic lateral sclerosis, or spinobulbar muscular atrophy, but the muscle atrophy is not limited to these.

Figure 1:
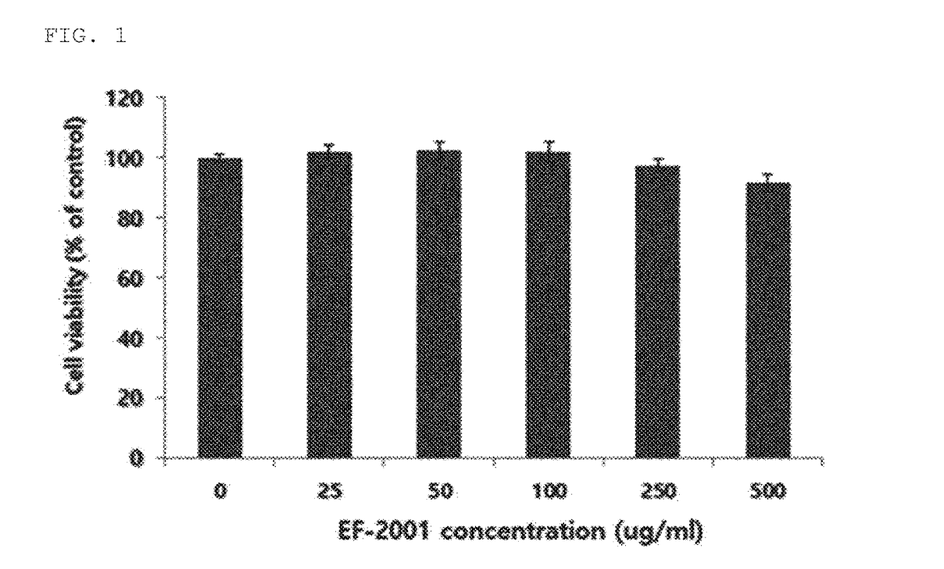
FIG. 1 is a diagram for confirming cytotoxicity of *Enterococcus faecalis* EF-2001.
Figure 2:
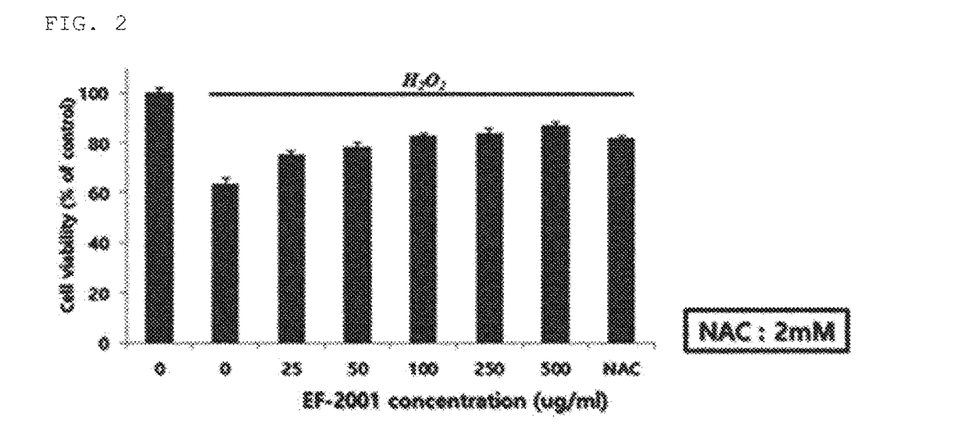
FIG. 2 is a diagram for confirming an effect of *Enterococcus faecalis* EF-2001 on damage to muscle cells induced by oxidative stress. NAC denotes a N-acetyl cysteine-treated group which is a positive control group.

In specific Experimental Examples of the present invention, the present inventors have confirmed that killed *Enterococcus faecalis* EF-2001 is not cytotoxic (see FIG. 1) and have confirmed the effect that the survival rate of muscle cells is restored depending on the concentration of killed *Enterococcus faecalis* EF-2001 when the muscle cells are treated with the killed *Enterococcus faecalis* EF-2001 in the damage to muscle cells induced by oxidative stress (see FIG. 2). In addition, the change in the amounts of HSP70 and SOD1 proteins in cells to which killed *Enterococcus faecalis* EF-2001 have been added are measured, and as a result, it has been found that killed *Enterococcus faecalis* EF-2001 induces muscle atrophy inhibition by increasing the expression levels of HSP70 and SOD1 proteins in muscle cells (see FIGS. 3 and 8). It has been confirmed that the decreased muscle mass is restored again after sarcopenia-induced mice have ingested killed *Enterococcus faecalis* EF-2001 (see FIGS. 4 to 6). In addition, it has been confirmed that killed *Enterococcus faecalis* EF-2001 is resistant to cell death, which is oxidative damage, and structural changes of cells by temporarily eliminating cell death induced by oxidative stress and increased radicals in muscle cells (see FIG. 7).

Consequently, killed *Enterococcus faecalis* EF-2001 of the present invention does not exhibit cytotoxicity and exhibits a remarkable muscle atrophy treatment effect by inhibiting the damage to muscle cells induced by oxidative stress, and thus *Enterococcus faecalis* EF-2001 of the present invention, a culture solution thereof, or a killed body thereof can be usefully used as an active ingredient in a pharmaceutical composition for prevention and treatment of muscle weakness-related diseases such as muscle atrophy and sarcopenia.

The composition according to the present invention is administered in a pharmaceutically effective amount. In the present invention, the "pharmaceutically effective amount" refers to an amount sufficient to treat a disease at a reasonable benefit or risk ratio applicable to medical treatment, and the effective dose level can be determined depending on the kind of patient's disease, severity, drug activity, sensitivity to drug, time of administration, route of administration and rate of excretion, duration of treatment, factors including co-drugs, and other factors well known in the medical field. The composition of the present invention may be administered as an individual therapeutic agent or in combination with other therapeutic agents, may be administered sequentially or simultaneously with conventional therapeutic agents, and may be administered in a single or multiple manner. It is important to administer the composition in an amount so that the maximum effect can be attained in a minimal amount without side effects in consideration of all the above factors, and the amount can be easily determined by those skilled in the art.

Specifically, the effective amount of the composition according to the present invention may vary depending on the patient's age, sex, and weight. In general, the composition may be administered in an amount of 0.1 mg to 100 mg, preferably 0.2 mg to 17 mg per 1 kg weight daily or every other day or one to three times a day. However, the effective amount may increase or decrease depending on the route of administration, severity of obesity, sex, weight, age, and the like, and thus the dosage does not limit the scope of the present invention in any way.

When formulating the composition, the composition is prepared using diluents or excipients such as fillers, extenders, binders, wetting agents, disintegrating agents, and surfactants which are commonly used.

Solid preparations for oral administration include tablets, pills, powders, granules, capsules, troches, and the like. Such solid preparations are prepared by mixing at least one or more excipients, for example, starch, calcium carbonate, and sucrose or lactose or gelatin with killed lactic acid bacterium *Enterococcus faecalis* EF-2001 of the present invention. In addition, lubricants such as magnesium stearate and talc are also used in addition to simple excipients. Liquid preparations for oral administration include suspensions, intravenous solutions, emulsions or syrups, and the like. The liquid preparations may contain various excipients, for example, wetting agents, sweeteners, fragrances, and preservatives in addition to water and liquid paraffin which are commonly used simple diluents.

Preparations for parenteral administration include sterilized aqueous solutions, non-aqueous solvents, suspension solvents, emulsions, freeze-dried preparations, suppositories, and the like.

As non-aqueous solvents and suspension solvents, propylene glycol, polyethylene glycol, vegetable oils such as olive oil, and injectable esters such as ethyl oleate, and the like may be used. As a base for suppositories, witepsol, macrogol, tween 61, cacao butter, laurin-based oil, glycerol, gelatin, and the like may be used.

The present invention also provides a food composition for prevention and improvement of muscle weakness-related diseases containing *Enterococcus faecalis*, a culture solution thereof, or a killed body thereof as an active ingredient.

In the present invention, the muscle weakness-related diseases mean all diseases which can be developed due to muscle weakness, and examples thereof include, but are not limited to, sarcopenia or muscle atrophy.

The sarcopenia refers to a gradual decrease in skeletal muscle mass with aging and means a state in which a decrease in muscle strength is directly caused and, as a result, various physical functions may be diminished and disorders may occur.

The muscle atrophy is preferably muscle atrophy due to the loss of muscle tissue caused as of muscles are not used, muscle atrophy due to the disease of muscle itself, or muscle atrophy due to the damage to nerves which dominate muscles. The muscle atrophy due to the loss of muscle tissue caused as muscles are not used is more preferably disuse atrophy, the muscle atrophy due to the disease of muscle itself is more preferably myasthenia gravis or dystrophy, and the muscle atrophy due to the damage to nerves which dominate muscles is more preferably spinal muscular amyotrophy, amyotrophic lateral sclerosis, or spinobulbar muscular atrophy, but the muscle atrophy is not limited to these.

Consequently, killed *Enterococcus faecalis* EF-2001 of the present invention or a culture solution thereof does not exhibit cytotoxicity and exhibits a remarkable sarcopenia or muscle atrophy prevention and treatment effect by inhibiting the damage to muscle cells induced by oxidative stress, and thus *Enterococcus faecalis* EF-2001 of the present invention, a culture solution thereof, or a killed body thereof can be used as an active ingredient in a food composition for prevention and improvement of muscle weakness-related diseases.

There is no particular limitation on the kind of food to which the killed lactic acid bacterium *Enterococcus faecalis* EF-2001 of the present invention is added. Examples of the food to which the substance can be added include health drinks, meat, sausage, bread, biscuits, rice cakes, chocolate, candy, snacks, confectionery, pizza, ramen, other noodles, gums, dairy products including ice cream, various soups, beverages, alcoholic beverages and vitamin complexes, and dairy products and processed dairy products and include both processed food and health functional food in the ordinary sense.

When the food composition according to the present invention is a beverage composition, there is no particular limitation on other ingredients except that the essential ingredient contains the compound at a predetermined proportion, and the beverage composition may contain various flavoring agents, natural carbohydrates, or the like as additional ingredients as ordinary beverages. Examples of the natural carbohydrates described above include monosaccharides, for example, glucose and fructose; disaccharides, for example, maltose and sucrose; and polysaccharides, for example, conventional sugars such as dextrin and cyclodextrin and sugar alcohols such as xylitol, sorbitol, and erythritol. As flavoring agents other than those described above, natural flavoring agents (taumatin, stevia extract, rebaudioside A, glycyrrhizine and the like) and synthetic flavoring agents (saccharin, aspartame, and the like) may be advantageously used. The proportion of natural carbohydrate is generally about 1 g to 20 g, preferably about 5 g to 10 g per 100 g of the composition of the present invention.

The present invention also provides a food additive for the prevention and improvement of muscle weakness-related diseases containing *Enterococcus faecalis*, a culture solution thereof, or a killed body thereof as an active ingredient.

The food additive according to the present invention may contain various nutrients, vitamins, minerals (electrolytes), flavors such as synthetic flavors and natural flavors, colorants and appetizers (cheese, chocolate and the like), pectic acid and salts thereof, alginic acid and salts thereof, organic acids, protective colloidal thickeners, pH adjusting agents, stabilizers, antiseptics, glycerin, alcohols, and carbonating agents used in carbonated beverages. The food additive may contain natural fruit juice and pulp for the preparation of fruit juice beverages and vegetable beverages in addition to these. These ingredients may be used independently or in combination. The proportion of these additives added is not limited but is generally selected from a range of 0.1 to 20 parts by weight per 100 parts by weight of linoleic acid of the present invention.

Killed *Enterococcus faecalis* EF-2001 of the present invention may be added to food as it is or used with other foods or food ingredients and may be suitably used according to conventional methods. The amount of the active ingredient added may be appropriately determined depending on the purpose of use (for prevention or improvement). In general, the amount of the composition of the present invention in the health functional food may be 0.1 to 90 parts by weight per part by weight of the entire food. However, in the case of long-term ingestion for health and hygiene purposes or for health control purposes, the amount may be equal to or less than the above range, and the active ingredient may be used in an amount equal to or more than the above range since the active ingredient does not have any problem in terms of safety.

In addition, the present invention provides a method for treating or preventing muscle weakness-related diseases including administering a pharmaceutically effective amount of *Enterococcus faecalis*, a culture solution, or a killed body thereof to an individual suffering from a muscle weakness-related disease or an individual.

The individual means human or non-human organisms, for example, non-human mammals such as cows, monkeys, birds, cats, mice, rats, hamsters, pigs, dogs, rabbits, sheep, and horses, and the treatment may be utilized for individuals with wounds or damaged skin tissues.

In addition, the treatment may be performed through oral administration or parenteral administration (for example, intramuscularly, intravenously, intraperitoneally, subcutaneously, intradermally, or topically applied) depending on the intended method. The dosage depends on the patient's condition and weight, the degree of disease, the drug form, and the route and time of administration but can be appropriately selected by those skilled in the art.

EMBODIMENTS

Hereinafter, the present invention will be described in detail with reference to Examples, Experimental Examples, and Preparation Examples.

However, the following Examples, Experimental Examples, and Preparation Examples are merely illustrative of the present invention, and the contents of the present invention are not limited to the following Examples, Experimental Examples, and Preparation Examples.

<Example 1> Preparation of Killed *Enterococcus faecalis* EF-2001

Killed *Enterococcus faecalis* EF-2001 used in the present invention were produced and prepared as follows.

Specifically, *Enterococcus faecalis* EF-2001 was subjected to aerobic or anaerobic culture in a medium used for general lactic acid bacteria culture. After the starter culture, main culture was performed. The culture was performed for one to three days while maintaining a neutral or weakly acidic pH and a culture temperature of 20° C. to 40° C. When the fermentation proceeds so that the number of bacteria per g (gram) reaches 7.5 trillion or more based on the final raw material, the culture solution was powdered through a heat treatment and then a drying process.

<Example 2> Culture of Cell

Normal muscle cells (C2C12) were cultured in DMEM medium containing fetal bovine serum (FBS) at 5%. In other words, normal skeletal muscle cells were cultured in DMEM medium containing 10% FBS, 150 µg/ml of 7.5% $NaHCO_3$, 58.4 µg/ml of glutamine, and 4.4 µl/ml of antibiotic/antimycotics in a 75 $cm^2$ plastic flask (SPL life science Co., Ltd. Korea) under conditions of 37° C. and 5% $CO_2$. The cell strain was maintained through secondary culture one time every two to three days.

<Example 3> Quantification of Cell

The medium was removed from the 75 $cm^2$ plastic flask in which the cells were grown, and then the cells were washed with CMF-PBS (calcium magnesium free-phosphate buffered saline, pH 7.2), treated with 0.25% trypsin/EDTA to be removed from the bottom of the flask, neutralized with cell culture solution, and then centrifuged (1200 rpm, 5 min). The culture solution was added to the pellet of the remaining cells, and then inhalation with a sterile pipette was repeatedly performed to prepare a single cell suspension. The prepared cell suspension and trypan blue were mixed at a ratio of 1:1 and subjected to the measurement using a hemocytometer under an optical microscope.

<Experimental Example 1> Confirmation of Cytotoxicity (Cell Viability) of Killed *Enterococcus faecalis* EF-2001

To measure the toxicity of killed *Enterococcus faecalis* EF-2001 to muscle cells, the EzCytox kit was used. Specifically, normal muscle cells (C2C12) were dispensed in a 96 well plate to be $2 \times 10^4$ cells/well. This was cultured in an incubator under conditions of 37° C. and 5% $CO_2$, then linoleic acid at various concentrations of 0, 25, 50, 100, 250, and 500 μg/ml was added thereto, and the cells were cultured for 24 hours. The cytotoxicity of killed *Enterococcus faecalis* EF-2001 was determined by calculating the survival rate of the normal muscle cells cultured for 24 hours using the EzCytox kit.

As a result, as illustrated in FIG. 1, the muscle cells had a survival rate of 100% when killed *Enterococcus faecalis* EF-2001 was not added and the groups to which killed *Enterococcus faecalis* EF-2001 was added at various concentrations also had similar survival rates to that of the group to which linoleic acid was not added. Consequently, it has been confirmed that killed *Enterococcus faecalis* EF-2001 of the present invention does not exhibit cytotoxicity to muscle cells (FIG. 1).

<Experimental Example 2> Confirmation of Effect of Killed *Enterococcus faecalis* EF-2001 on Damage to Muscle Cell Induced by Oxidative Stress In order to confirm the effect of killed EF-2001 at various concentrations on $H_2O_2$-induced apoptosis, muscle cells were first placed in a 96 well plate to be $2 \times 10^4$ cells/well and cultured for 24 hours under conditions of 37° C. and 5% $CO_2$. Thereafter, killed *Enterococcus faecalis* EF-2001 was added thereto at concentrations of 0, 25, 50, 100, 250, and 500 μg/ml, respectively. The total volume was adjusted to 195 μl with 10% FBS-DMEM medium and the muscle cells were cultured in an incubator for 24 under conditions of 37° C. and 5% $CO_2$. $H_2O_2$ was added to this culture solution at a concentration of 1 mM so that the total volume was 200 μl, and then the muscle cells were cultured for another 120 minutes. After culture, 10 μl of the EzCytox kit was added to the culture solution, and the absorbance was measured after 1 hour to determine the effect.

As a result, it has been confirmed that the muscle cells had a survival rate of 100% when $H_2O_2$ was not added and the survival rate of muscle cells decreases when the muscle cells were treated with $H_2O_2$ as illustrated in FIG. 2. In addition, the effect has been confirmed that the survival rate of muscle cells is restored depending on the concentration of killed *Enterococcus faecalis* EF-2001 when the muscle cells are treated with the killed *Enterococcus faecalis* EF-2001 (FIG. 2).

Consequently, it has been confirmed that killed *Enterococcus faecalis* EF-2001 significantly restores the damage to muscle cells induced by oxidative stress in a concentration-dependent manner.

<Experimental Example 3> Comparison of Change in Expression of HSP70 (Heat Shock Protein) and SOD1 Proteins Changes in the amounts of HSP70 (Heat Shock Protein) and SOD1 proteins in the cells of the addition group to which killed *Enterococcus faecalis* EF-2001 was added were measured using a western blot. In other words, normal muscle cells (C2C12) were dispensed in a 96 well plate to be $5 \times 10^4$ cells/well and then cultured in an incubator under conditions of 37° C. and 5% $CO_2$. Thereafter, 25 μg/ml of killed *Enterococcus faecalis* EF-2001 was added thereto, then the total volume was adjusted to 2 ml with 10% FBS-DMEM medium, and the cells were cultured for 24 under conditions of 37° C. and 5% $CO_2$. $H_2O_2$ was added to this culture solution at a concentration of 1 mM so that the total volume was 2 ml, then the cells were cultured for another 60 minutes, and then the cells were crushed to obtain proteins. The expression levels of HSP70 protein and SOD1 protein were detected using HSP70, SOD1, and beta-actin antibodies using western blot.

Figure 3:
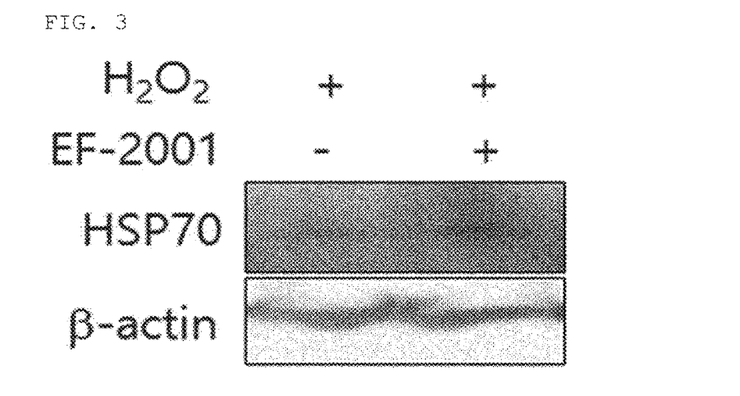
FIG. 3 is a diagram for confirming a change in expression of HSP70 (Heat Shock Protein) in muscle cells in an oxidative stress environment by *Enterococcus faecalis* EF-2001.
Figure 4:
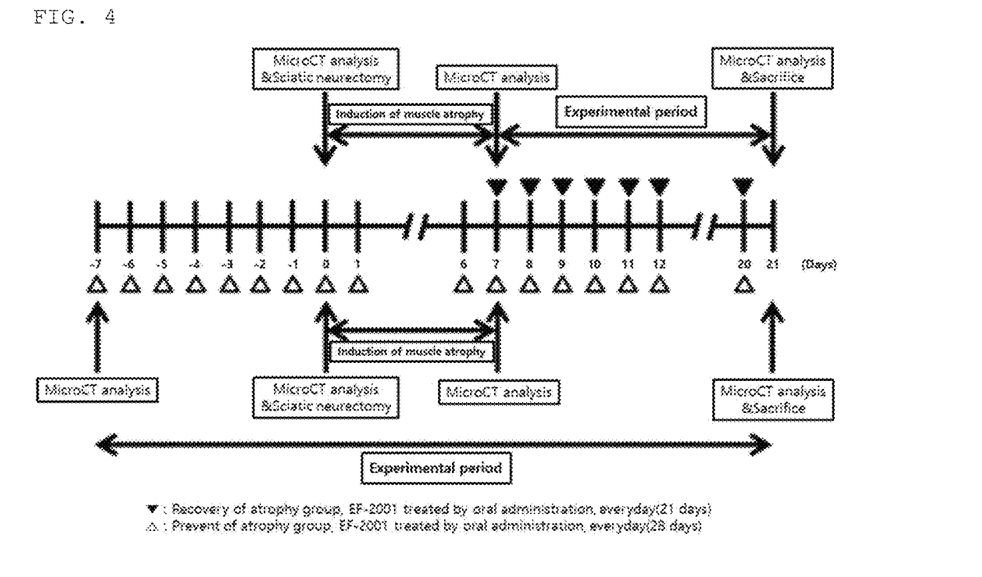
FIG. 4 is a diagram illustrating time and experimental plan of oral administration of *Enterococcus faecalis* EF-2001 at two different concentrations of 2 mg/kg and 30 mg/kg after surgery to induce muscle atrophy by excising the right hind limb arch of a mouse and thus limiting muscle movement.
Figure 8:
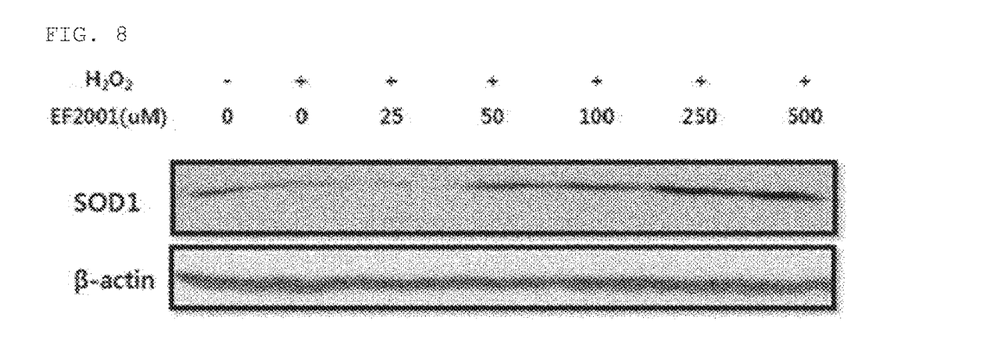
FIG. 8 is a diagram for confirming a change in expression of SOD1 protein in muscle cells in an oxidative stress environment by *Enterococcus faecalis* EF-2001.

As a result, the expression levels of HSP70 and SOD1 proteins in the addition group to which killed *Enterococcus faecalis* EF-2001 was added were restored to those in normal cells as illustrated in FIGS. 3 and 8. In other words, it has been confirmed that the effect of protecting muscle cells from oxidative stress is exerted through the expression of HSP70. In addition, it has been confirmed that killed *Enterococcus faecalis* EF-2001 decreases free radicals of reactive oxygen which is oxidative stress to restore the expression of SOD1 which appears with respect to reactive oxygen.

Consequently, it has been confirmed that the present killed *Enterococcus faecalis* EF-2001 can prevent muscle atrophy by causing increased expression of HSP70 and SOD1 proteins in muscle cells (FIGS. 3 and 8).

<Experimental Example 4> Comparison of Restoring Ability of Sarcopenia-Induced Mice from Sarcopenia after Ingestion of Killed *Enterococcus faecalis* EF-2001

In order to confirm the effect of preventing and restoring muscle atrophy by killed *Enterococcus faecalis* EF-2001, muscle images were acquired using a micro tomography apparatus to measure the initial muscle mass before induction of muscle atrophy.

Specifically, in order to induce muscle atrophy, the right hind limb arch of a mouse was excised to limit muscle movement and thus to induce muscle atrophy. In the design illustrated in FIG. 4, *Enterococcus faecalis* EF-2001 was ingested to the mouse by an oral administration method at two concentrations of 2 mg/kg and 30 mg/kg. The prevented group ingested *Enterococcus faecalis* EF-2001 every day from one week before the surgery to induce muscle atrophy and the treated group ingested *Enterococcus faecalis* EF-2001 every day for three weeks after the surgery to induce muscle atrophy. In 3 weeks after the surgery, muscle images were acquired using a microscopic tomography apparatus and illustrated in FIG. 5, and the comparative analysis on the influence of *Enterococcus faecalis* EF-2001 ingestion on muscle atrophy and differences was performed based on the photographed images.

Figure 5:
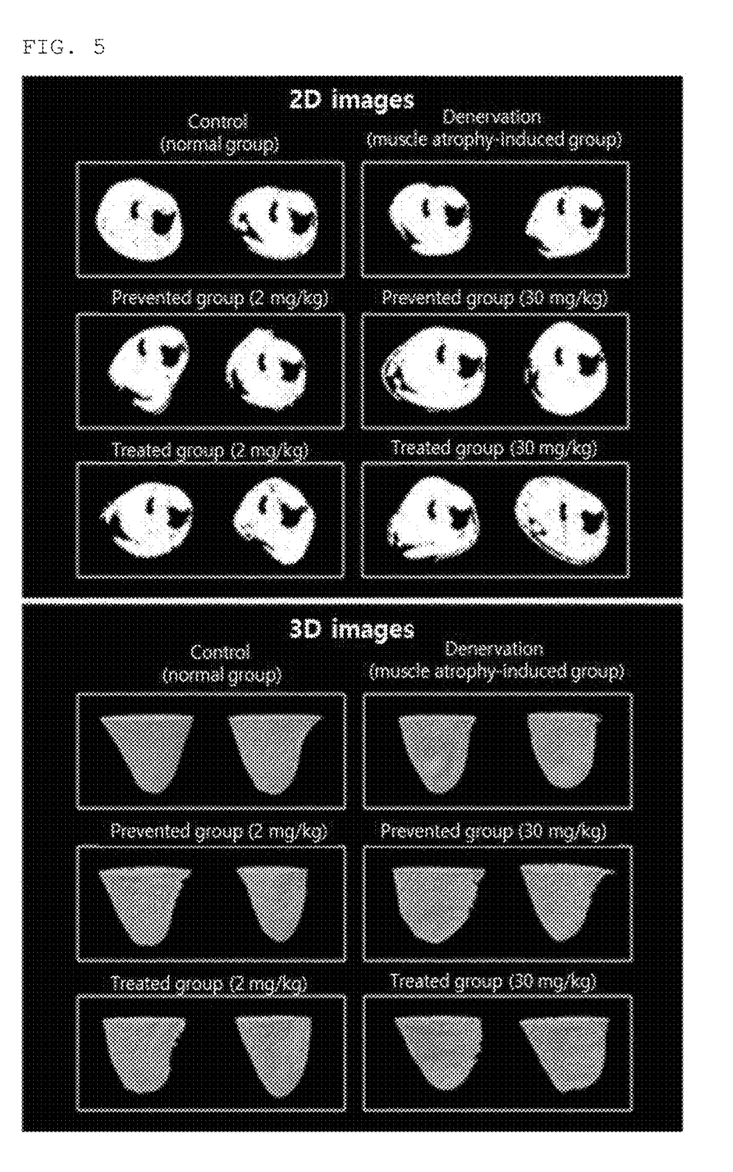
FIG. 5 is a diagram illustrating, after surgery to induce muscle atrophy by excising the right hind limb arch of a mouse and thus limiting muscle movement, muscle images of a prevented group which has ingested *Enterococcus faecalis* EF-2001 every day from one week before and a treated group which has ingested *Enterococcus faecalis* EF-2001 every day for three weeks after the surgery taken using a micro tomography apparatus in three weeks after the surgery.
Figure 6:
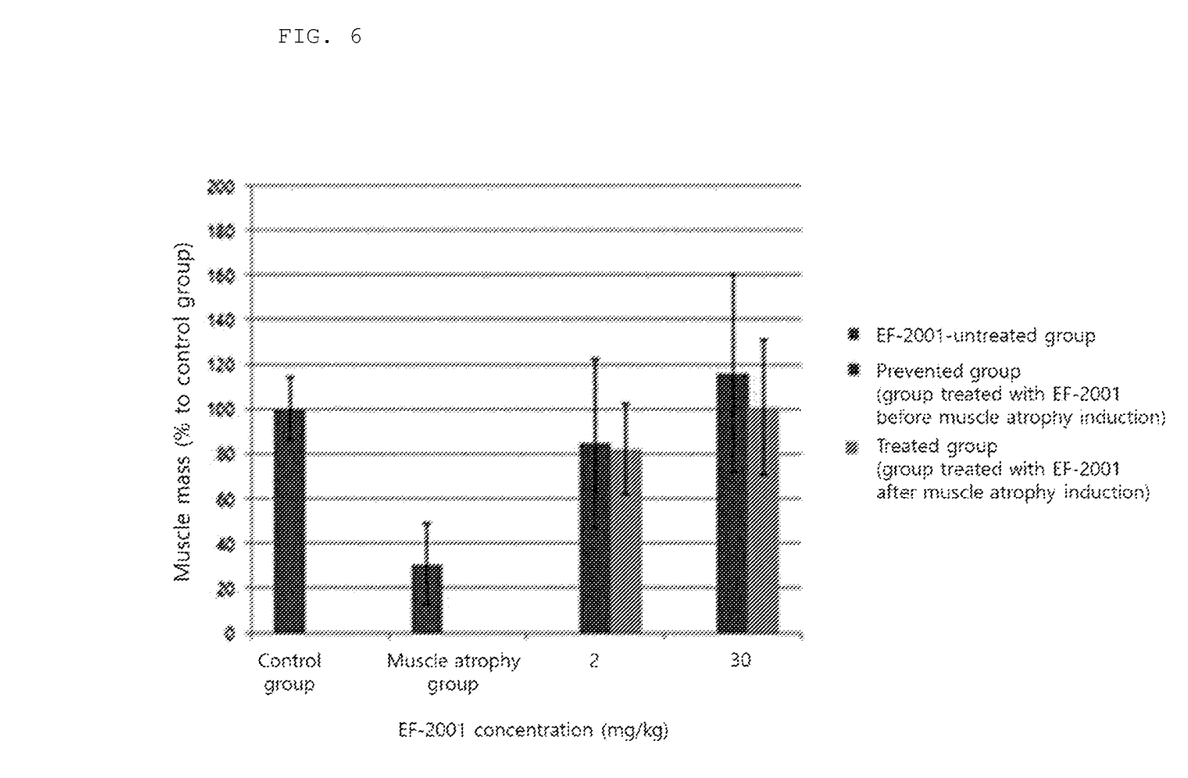
FIG. 6 is a diagram illustrating results of comparative analysis on influence of *Enterococcus faecalis* EF-2001 ingestion on muscle atrophy and differences based on the images illustrated in FIG. 5.

As a result, it has been confirmed that the muscle mass of the *Enterococcus faecalis* EF-2001-ingested group was restored as compared to the muscle atrophy group (denervation) when *Enterococcus faecalis* EF-2001 was ingested for three to four weeks as illustrated in FIG. 6 (FIGS. 5 and 6).

<Experimental Example 5> Confirmation of Effect of Killed *Enterococcus faecalis* EF-2001 on Muscle Cell Apoptosis Induced by Oxidative Stress The effect of killed *Enterococcus faecalis* EF-2001 on $H_2O_2$-induced cell death was confirmed through changes in chromatin condensation and fragmentation morphology by DAPI fixation staining.

Figure 7:
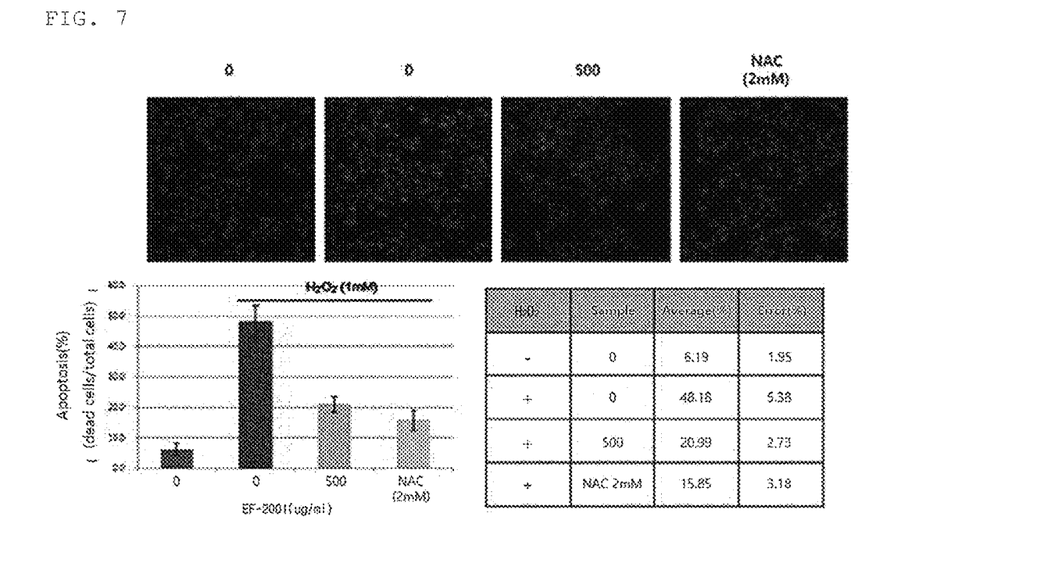
FIG. 7 is a diagram for confirming an effect of killed *Enterococcus faecalis* EF-2001 on $H_2O_2$-induced cell death.

Specifically, the number of cells in the chromatin condensation and fragmentation morphology in the experimental group treated with $H_2O_2$ was higher than in the control group which was not treated with $H_2O_2$, and it has been confirmed that the number of cells in the chromatin condensation and fragmentation morphology decreases in a concentration-dependent manner in the group treated with killed *Enterococcus faecalis* EF-2001 at various concentrations (FIG. 7). In the case of muscle cells induced with $H_2O_2$, the protein or DNA is damaged as a high radical concentration in the cells is maintained, and this induces cell death by causing oxidation in the outer cell membrane, intracellular structural protein, nuclear DNA and the like and thus causing damage due to structural changes.

Consequently, it has been confirmed that killed *Enterococcus faecalis* EF-2001 is resistant to cell death, which is oxidative damage, and structural changes of cells by temporarily eliminating cell death induced by oxidative stress and increased radicals in muscle cells through this experiment.

<Preparation Example 1> Preparation of Medicine

1. Preparation of Powder
Killed *Enterococcus faecalis* EF-2001 of the present invention: 1 mg to 10 g
Lactose: 1 g
A powder was prepared by mixing the above ingredients together and filling the mixture in a gas-tight bag.

2. Preparation of Tablet
Killed *Enterococcus faecalis* EF-2001 of the present invention: 1 mg to 10 g
Corn starch: 100 mg
Lactose: 100 mg
Magnesium stearate: 2 mg
A tablet was prepared by mixing the above ingredients together and then tableting the mixture according to a conventional method for preparing tablets.

3. Preparation of Capsule
Killed *Enterococcus faecalis* EF-2001 of the present invention: 1 mg to 10 g
Corn starch: 100 mg
Lactose: 100 mg
Magnesium stearate: 2 mg
A capsule was prepared by mixing the above ingredients together and then filling the mixture in a gelatin capsule according to a conventional method for preparing capsules.

4. Preparation of Injection
Killed *Enterococcus faecalis* EF-2001 of the present invention: 1 mg to 10 g
Mannitol: 180 mg
$Na_2.HPO_4.2H_2O$: 26 mg
Distilled water: 2974 mg
An injection containing the above ingredients in predetermined amounts was prepared according to a conventional method for preparing an injection.

<Production Example 2> Preparation of Health Food

1. Preparation of Health Food
Killed *Enterococcus faecalis* EF-2001 of the present invention: 1 mg to 10 g
Vitamin mixture: suitable amount
Vitamin A acetate: 70 µg
Vitamin E: 1.0 mg
Vitamin: 0.13 mg
Vitamin B2: 0.15 mg
Vitamin B6: 0.5 mg
Vitamin B12: 0.2 µg
Vitamin C: 10 mg
Biotin: 10 µg
Nicotinic acid amide: 1.7 mg
Folic acid: 50 mg
Calcium Pantothenate: 0.5 mg
Inorganic mixture: suitable amount
Ferrous sulfate: 1.75 mg
Zinc oxide: 0.82 mg
Magnesium carbonate: 25.3 mg
Potassium dihydrogen phosphate: 15 mg
Calcium hydrogen phosphate: 55 mg
Potassium citrate: 90 mg
Calcium carbonate: 100 mg
Magnesium chloride: 24.8 mg
The composition ratio of the vitamin and mineral mixtures was adjusted by mixing ingredients relatively suitable for health food in a preferred embodiment, but the mixing ratio may be arbitrarily modified. The above ingredients may be mixed together according to a conventional method for preparing health food, then prepared into granules, and used in the preparation of a health food composition according to a conventional method.

2. Preparation of Health Drink
Killed *Enterococcus faecalis* EF-2001 of the present invention: 1 mg to 10 g
Citric acid: 1000 mg
Oligosaccharide: 100 g
Plum concentrate: 2 g
Taurine: 1 g
Total with purified water: 900 ml
A solution obtained by mixing the above ingredients together according to a conventional method for preparing a health drink and then stirring and heating the mixture at 85° C. for about 1 hour was filtered, collected in a sterilized container, sealed and sterilized, then stored in a refrigerator, and then used in the preparation of a health drink composition.

The composition ratio was adjusted by mixing ingredients relatively suitable for favorite beverages in a preferred embodiment, but the mixing ratio may be arbitrarily modified according to regional and ethnic preferences such as class of demand, country of use, and usage.

The invention claimed is:

1. A method for treating a muscle weakness-related disease comprising administering a killed body of *Enterococcus faecalis* EF-2001 to an individual suffering from a muscle weakness-related disease, thereby treating said muscle weakness-related disease in said individual.

2. The method for treating a muscle weakness-related disease according to claim 1, wherein the killed body of *Enterococcus faecalis* EF-2001 is obtained by subjecting *Enterococcus faecalis* EF-2001 to starter culture, then subjecting the *Enterococcus faecalis* EF-2001 to main culture in a neutral or acidic medium in a temperature range of 20° C. to 40° C., and then performing a heat treatment.

3. The method for treating a muscle weakness-related disease according to claim 1, wherein the killed body of *Enterococcus faecalis* EF-2001 increases expression of HSP70 protein or SOD1 protein in a muscle cell.

4. The method for treating a muscle weakness-related disease according to claim 1, wherein the disease is sarcopenia or muscle atrophy.

5. The method for treating a muscle weakness-related disease according to claim 4, wherein the muscle atrophy is a disease selected from the group consisting of disuse atrophy, myasthenia gravis, spinal muscular amyotrophy, amyotrophic lateral sclerosis, and spinobulbar muscular atrophy.

6. The method for treating a muscle weakness-related disease according to claim 1, wherein the killed body of *Enterococcus faecalis* EF-2001 is prepared in a form selected from the group consisting of a capsule, a tablet, a powder, a granule, a liquid, a pill, a flake, a paste, a syrup, a gel, a jelly, and a bar.

7. The method of claim 1, wherein the killed body of *Enterococcus faecalis* EF-2001 is administered to the individual in an amount ranging from 0.1 mg/kg and 100 mg/kg once a day or every other day.

* * * * *